(12) United States Patent
Dandala et al.

(10) Patent No.: US 6,903,232 B2
(45) Date of Patent: Jun. 7, 2005

(54) PROCESS FOR THE PREPARATION OF A HIGHLY PURE PHARMACEUTICAL INTERMEDIATE, 4-(CYCLOPROPYLCARBONYL)-α, α-DIMETHYLPHENYLACETIC ACID

(75) Inventors: Ramesh Dandala, Hyderabad (IN); Umashankar Das, Saskatoon (CA); Divvela Venkata Naga Srinivasa Rao, Hyderabad (IN); Meenakshisunderam Sivakumaran, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 0 days.

(21) Appl. No.: 10/612,637

(22) Filed: Jul. 2, 2003

(65) Prior Publication Data

US 2004/0077900 A1 Apr. 22, 2004

(30) Foreign Application Priority Data

Jun. 19, 2002 (IN) .................................. PCT/IN02/00135

(51) Int. Cl.$^7$ ............................................. C07C 229/00
(52) U.S. Cl. .......................... 562/450; 560/51; 560/52; 562/555
(58) Field of Search .......................... 562/50, 555, 450; 560/51, 52

(56) References Cited

U.S. PATENT DOCUMENTS 5,581,011 A * 12/1996 D'Ambra .................. 560/8
5,663,412 A * 9/1997 D'Ambra ................. 560/51

* cited by examiner

Primary Examiner—Rita Desai
Assistant Examiner—Hector M. Reyes
(74) Attorney, Agent, or Firm—Jay R. Akhave

(57) ABSTRACT

This invention relates to a novel process to obtain highly pure 4-(cyclopropylcarbonyl)-α,α-dimethylphenylacetic acid of Formula I through crystallization from a mixture of para and meta regioisomers of Formula I and II in cyclohexane, whereby the amount of undesired meta isomer, 3-(cyclopropylcarbonyl)-α,α-dimethylphenylacetic acid of Formula II

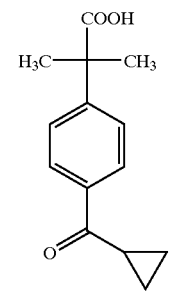

Formula I

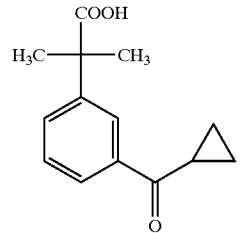

Formula II is decreased to below 0.5%. The compound of Formula I is a key intermediate for the preparation of high purity terfenadine carboxylate, which is a known antihistaminic.

6 Claims, No Drawings

PROCESS FOR THE PREPARATION OF A HIGHLY PURE PHARMACEUTICAL INTERMEDIATE, 4-(CYCLOPROPYLCARBONYL)-α, α-DIMETHYLPHENYLACETIC ACID

CROSS REFERENCE TO RELATED APPLICATIONS

Indian Patent Application Filing Date Jun. 25, 2001
Application No. 511/MAS/2001
Status Not Issued
PCT Application Filing Date Jun. 19, 2002
Application No. PCT/IN02/00135
Publication Date Jan. 03, 2003
Publication No. WO 03/000658 A1

STATEMENTS REGARDING FEDERALLY SPONSORED RESEARCH AND DEVELOPMENT

None.

BACKGROUND OF THE INVENTION

This invention relates to a process for the preparation of highly pure 4-(cyclopropylcarbonyl)-α,α-dimethylphenylacetic acid of Formula I, a key intermediate useful in the preparation of highly pure Terfenadine carboxylate.

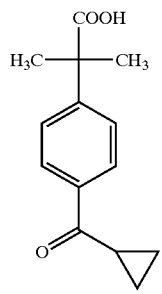

Formula I

Terfenadine carboxylate is a non-sedative antihistaminic compound. It is reported to be a specific $H_2$-receptor antagonist that is also devoid of any anticholinergic, antiserotoninergic, and antiadrenergic effects.

Piperidine derivatives related to terfenadine carboxylate are disclosed in U.S. Pat. No. 4,254,129 and U.S. Pat. No. 4,254,130. In these patents, α,α-dimethyl-4-[1-hydroxy-4-[4-(hydroxydiphenyl methyl)-1-piperidinyl]butyl]benzeneacetic acid of Formula III

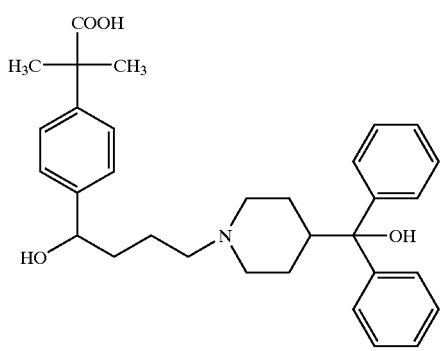

Formula III is prepared by alkylation of a substituted piperidine derivative of Formula IV

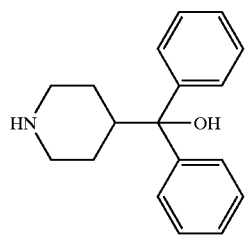

Formula IV with an ω-haloalkyl substituted phenyl ketone of Formula V

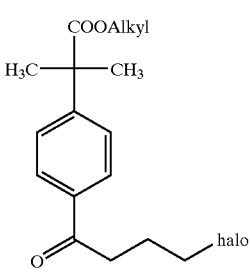

Formula V wherein halo is a halogen atom, such as, chlorine, bromine or iodine, and alkyl moiety has from 1 to 6 carbon atoms and is straight or branched, followed by reduction of the ketone group and subsequent base hydrolysis.

Preparation of compounds of Formula V is achieved by reacting α,α-dimethylphenylacetic acid alkyl esters with 4-halobutyryl halide under general conditions of Friedel-Crafts acylation. U.S. Pat. No. 4,254,130 describes the preparation of ethyl 4-(4-chloro-1-oxobutyl)-α,α-dimethylphenylacetate by reaction of 4-chlorobutyryl chloride, aluminum chloride and ethyl α,α-dimethylphenylacetate in carbon disulfide. However, the described reaction results in virtually inseparable mixture of monosubstituted aromatic para and meta regioisomers of the Formula VI where unwanted meta isomer predominates to about 65%.

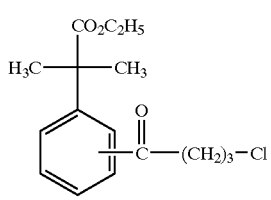

Formula VI

Mixture of para and meta regioisomers

CA Patent 2,118,188 discloses a process, which has proved to be more selective in the formation of para isomer. In this process, Friedel-Crafts acylation has been carried out on the derivative of Formula VII with 4-chlorobutyryl chloride as the acylating agent in carbon disulfide Formula VII

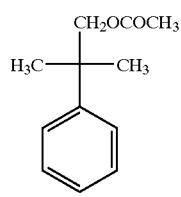

in the presence of aluminum chloride and the corresponding para acylated product has been obtained that contains no more than 10% of meta isomer. The presence of meta isomer at this stage results in an unacceptable level of meta isomer in terfenadine carboxylate and once again it is difficult to achieve pharmaceutically pure product from such a mixture. This requires time consuming purification processes which are wasteful of material and costly.

U.S. Pat. No. 5,578,610 provides a procedure wherein the mixture of regioisomers of Formula VI has been transformed to another mixture of para and meta regioisomers of Formula VIII and Formula VIII

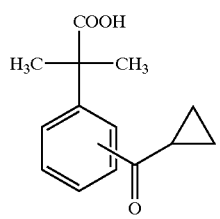

Mixture of para and meta regioisomers subsequently the substantially pure para regioisomer is obtained by fractional crystallization of the corresponding cinchonidine salt. This process exhibits several disadvantages such as use of expensive cinchonidine, its toxicity, low yield and in addition to that, two isolation steps are necessary to obtain the desired product of Formula I.

U.S. Pat. No. 6,147,216 provides an alternate technique to obtain enriched para regioisomer by high vacuum fractional distillation of methyl or ethyl ester of the mixture of isomeric acids of Formula VIII followed by repeated fractional crystallization at low temperatures. This process is operationally tedious, inefficient, yields are low and therefore, is not amenable to industrial scale.

The aim of the present invention is to provide an efficient method to obtain highly pure 4-(cyclopropylcarbonyl)-α,α-dimethylphenylacetic acid of Formula I, which is an useful intermediate for the preparation of pharmaceutically highly pure antihistaminic piperidine derivatives.

DETAILED DESCRIPTION OF THE INVENTION

The instant invention relates to a novel process to produce highly pure para regioisomer 4-(cyclopropylcarbonyl)-α,α-dimethylphenylacetic acid, of Formula I whereby the amount of meta isomer, 3-(cyclopropylcarbonyl)-α,α-dimethylphenylacetic acid, of Formula II is decreased to below 0.5%.

Specifically the present invention involves treating 1-acetoxy-2-methyl-2-phenylpropane, of Formula VII in methylene chloride with 4-chlorobutyryl chloride and anhydrous aluminium chloride to obtain a mixture of regioisomers, of Formula IX that contains greater than 80% of para isomer.

Formula IX

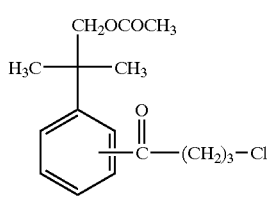

Mixture of para and meta regioisomers

This mixture of regioisomers is hydrolyzed under conditions effective to produce a mixture of regioisomers of Formula X. Typically this reaction is carried out by a base hydrolysis procedure which is well known in the art. The intermediate hydroxy compound is then oxidized Formula X

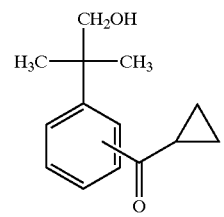

Mixture of para and meta regioisomers to give the corresponding carboxylic acid regioisomers, of Formula VIII using, for example, potassium permanganate. The potassium permanganate oxidation is carried out in a Formula VIII

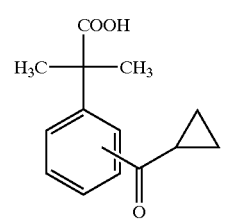

Mixture of para and meta regioisomers suitable acidic medium such as acetic acid/acetone at a temperature ranging from room temperature to 60° C. Other suitable reagents for the oxidation are, chromium (IV) oxide, sodium periodate, m-chloroperbenzoic acid and nitric acid.

According to the present invention, the above mixture of para and meta regioisomers of formula VIII is subjected to crystallization process to recover highly pure para regioisomer of Formula I. Such recovery is carried out by selective crystallization from a suitable solvent that include hexanes, heptane, cyclohexane, diethyl ether, diisopropyl ether and a mixture thereof. However, one may proceed preferably by using cyclohexane for crystallization.

Selective crystallization is achieved by dissolving a mixture of regioisomers of Formula VIII containing up to 20% of meta regioisomer in a solvent at a temperature ranging from 20° C. to reflux temperature of the solvent. The amount of solvent is at least 5 parts by volume per part of the mixture of regioisomers. Higher amounts of solvent and generally upto 20 parts by volume may be used. The aforesaid solution is then slowly cooled to 20–25° C. and the desired para regioisomer is obtained in highly pure form as a free flowing crystalline material which is isolated by filtration.

Major advantages realized in the present invention compared to the prior art are increased process productivity and product purity. The level of meta regioisomer under present crystallization conditions is reduced to less than 0.5% that enables the control of isomer purity in terfenadine carboxylate product. The process of the present invention is feasible commercially and simple on industrial scale.

The aforesaid highly pure para regioisomer of Formula I can be reacted with

Formula I

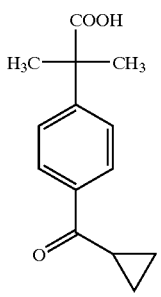

piperidine compound of Formula IV

Formula IV

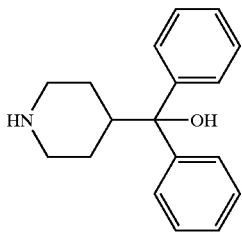

under the conditions effective to form the piperidine derivative compound of Formula XI Formula XI

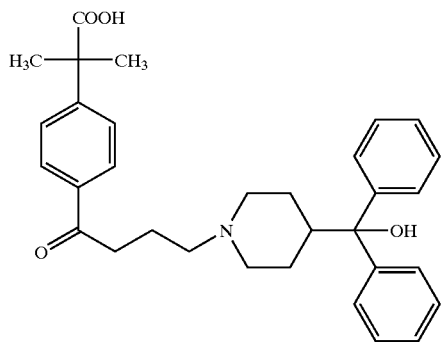

having a keto group which is converted to hydroxyl group by reduction to produce pharmaceutically highly pure terfenadine carboxylate of Formula III Formula III

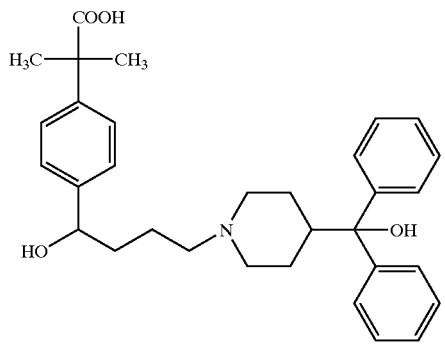

that contains less than 0.1% of meta regioisomer.

Further details of the present invention are to be found in the following examples without limiting it.

Example 1–3, known in the art, show the steps used to prepare the 80/20 mixture of 4-(CYCLOPROPYL-CARBONYL)α,α-DIMETHYLPHENYLACETIC ACID and 3-(CYCLOPROPYLCARBONYL)-α,α-DIMETHYL-PHENYLACETIC ACID. The subsequent processing of these mixtures to minimize the meta isomeric form and improve the desirable para isomeric content is detailed in the Examples 4–6. Example 7 and 8 show that one can use the pure para isomeric intermediate to make pharmaceutically pure terfenadine carboxylate.

EXAMPLE 1

Preparation of 1-Acetoxy-2-methyl-2-[4-(4-chlorobutyryl) phenyl]propane and 1-acetoxy-2-methyl-2-[3-(4-chlorobutyryl) phenyl]propane 1-Acetoxy-2-methyl-2-phenylpropane (100 g, 0.52 mol) was dissolved in methylene chloride (500 ml) at 20–25° C. under nitrogen atmosphere. The mass was cooled to −5° to −3° C. and 4-chlorobutyryl chloride (88 g, 0.62 mol) was added maintaining the temperature between −5° to −3° C. Aluminium chloride (138.5 g, 1.04 mol) was added in small lots at −5° to −3° C. and continued stirring for 3 hours at −5° to 0° C. Thereafter, second lot of aluminium chloride (34.62 g, 0.26 mol) was added in small lots at −5° to 0° C. After 6 hours stirring, the reaction mass was slowly added to a mixture of crushed ice (720 g) and conc. hydrochloric acid (100 ml) at a temperature below 25° C. Methylene chloride layer was separated and aqueous layer was extracted with methylene chloride (100 ml). The combined methylene chloride extract was washed with 5% aqueous sodium bicarbonate solution (100 ml). Methylene chloride was removed under reduced pressure at 20–30° C. to obtain an oily residue containing a mixture of para- and meta-isomers (approximately 80:20 ratio, by $^1$H NMR). Yield: 152 g.

$^1$H NMR (300 MHz) in CDCl$_3$: δ(ppm) 7.93 (d, 2H, J=9.0 Hz, Ar—H), 7.46 (d, 2H, J=9.0 Hz, Ar—H), 4.15 (s, 2H, CH$_2$—OCOCH$_3$), 3.69 (t, 2H, J=7.5 Hz, CH$_2$Cl), 3.17 (t, 2H, 7.5 Hz, COCH$_2$), 2.24 (m, 2H, COCH$_2$CH$_2$), 2.0 (s, 3H, COCH$_3$), 1.38 (s, 6H, 2×CH$_3$). The meta isomer is recognized by its signals at δ(ppm) 7.95 (m, 1H, Ar—H), 7.92 (m, 1H, Ar—H), 7.48 (m, 1H, Ar—H), 7.26 (m, 1H, Ar—H), 4.14 (s, 2H, CH$_2$—OCOCH$_3$), 3.62 (t, 2H, CH$_2$Cl), 2.57 (t, 2H, COCH$_2$), 2.21 (m, 2H, COCH$_2$CH$_2$).

EXAMPLE 2

Preparation of 2-[4-cyclopropylcarbonyl]phenyl-2-methyl propanol and 2-[3-cyclopropylcarbonyl] phenyl-2-methyl propanol Sodium hydroxide (61.2 g, 1.53 mol) was dissolved in methanol (600 ml) at 25–30° C. and product obtained in Example 1 (152 g, 0.51 mol) was added slowly at 25–30° C. Reaction mass was stirred at 25–30° C. for 2 hours and thereafter, methanol was removed at 40–60° C. under reduced pressure. The residue was cooled to 25–30° C. and DM water (300 ml) was added. Product was extracted with toluene (2×200 ml). The toluene extract was washed with DM water and toluene was removed at 55–70° C. under reduced pressure to obtain the title product as an oily residue. Yield: 100 g.

EXAMPLE 3

Preparation of 4-(cyclopropylcarbonyl)-α,α-dimethylphenylacetic acid and 3-(cyclopropylcarbonyl)-α,α-dimethylphenylacetic acid Substrate from Example 2 (100 g, 0.45 mol) was dissolved in acetone (300 ml) at 25–30° C. DM water (450 ml)

and glacial acetic acid (60 ml) were added. Potassium permanganate (153 g, 0.96 mol) was added in small lots in 2 hours maintaining the temperature at 25–30° C. Stirring was continued for 1 hour at 30–35° C. and thereafter, temperature was raised to 40–45°. After stirring for 2 hours the reaction mass was filtered through hyflo and the residue was washed with acetone (100 ml). The filtrate was concentrated at 40–45° C. under reduced pressure to remove acetone. To the concentrated mass, hydrochloric acid (90 ml) was added followed by sodium metabisulfite (21.37 g) and stirring continued at 20–25° C. for 30 minutes. The product was extracted with methylene chloride (2×200 ml). The combined methylene chloride extract was stirred with 800 ml of 5% w/w sodium hydroxide solution and aqueous layer was separated which was acidified to pH 1.8–2.0 at 10–12° C. by adding conc. hydrochloric acid. The title product was extracted with methylene chloride (2×150 ml). The methylene chloride extract was washed with DM water (80 ml) and methylene chloride was distilled at 40–45° C. under reduced pressure to obtain an oily residue (72 g) that contained para- and meta- isomers approximately in the ratio of 80:20 ($^1$H NMR).

$^1$H NMR (300 MHz) in CDCl$_3$: δ(ppm) 12.6 (1H, COO$\underline{H}$), 8.0 (d, 2H, Ar—$\underline{H}$), 7.5 (d, 2H, Ar—$\underline{H}$), 2.66 (m,1H, —CO$\underline{CH}$—), 1.66 (s, 6H, 2×C$\underline{H}_3$), 1.25 (m, 2H, C$\underline{H}_2$), 1.0 (m, 2H, C$\underline{H}_2$). The meta isomer is recognized by its signals at δ(ppm) 8.1 (m, 1H, Ar—$\underline{H}$), 7.92 (m, 1H, Ar—$\underline{H}$), 7.63 (m, 1H, Ar—$\underline{H}$), 7.46 (m, 1H, Ar—$\underline{H}$).

The regioisomers mixture thus obtained was subjected to crystallization to obtain highly pure 4-(cyclopropylcarbonyl)-α,α-dimethylphenylacetic acid as described in the following examples:

EXAMPLE 4

The mixture of regioisomers (100 g, 0.43 mol) obtained in accordance with Example 3 was dissolved in cyclohexane (1500 ml) at 60–65° C. The solution was seeded with 0.5 g of pure para regioisomer at 50–55° C. and was cooled to 15–18° C. slowly in 2 hours and during this period, the product crystallizes out. Stirring was continued at 15–18° C. for 1 hour to complete crystallization. The product was filtered, washed with cyclohexane (2×25 ml) and dried under reduced pressure at 35–40° C. to yield 72 g of highly pure crystalline para regioisomer, 4-(cyclopropylcarbonyl)-α,α-dimethylphenylacetic acid. mp: 84–88° C., $^1$H NMR (300 MHz) CDCl$_3$: δ(ppm) 12.6 (1H, COO$\underline{H}$), 8.0 (d, 2H, Ar—$\underline{H}$), 7.5 (d, 2H, Ar—$\underline{H}$), 2.66 (m, 1H, —CO$\underline{CH}$—), 1.66 (s, 6H, 2×C$\underline{H}_3$), 1.25 (m, 2H, C$\underline{H}_2$), 1.0 (m, 2H, C$\underline{H}_2$). The product contained 0.48% of meta isomer by HPLC.
HPLC CONDITIONS:
Column: 25 cm long, 4.0 mm internal diameter packed with β-cyclodextrin bonded to silica through amide linkage; particle size: 5 µm; column temperature: ambient
Detection wavelength: 254 nm
Mobile Phase: Mixture of acetate buffer pH 4.0 and acetonitrile in the ratio of 50:50 v/v. Acetate buffer pH 4.0 was prepared by adding 1.2 ml of acetic acid to 1000 ml water and pH adjusted to 4.0 with dilute aqueous ammonia.

EXAMPLE 5

The mixture of regioisomers approximately para:meta 80:20 (70 g, 0.30 mol) obtained from Example 3 was dissolved in cyclohexane (350 ml) at 60–65° C. Solution was cooled to 28–30° C. slowly in 2 hours. The product was collected by filtration and was suspended in cyclohexane (280 ml) and heated to 65–68° C. to obtain a clear solution. The solution was cooled to 25–28° C. to crystallize out the product which was filtered and washed with cyclohexane (2×20 ml) and dried under reduced pressure at 35–40° C. The product contained 0.27% meta isomer by HPLC. Yield: 51.1 g.

EXAMPLE 6

Substrate of Example 3 (50 g, 0.21 mol) was dissolved in diisopropyl ether (60 ml) and diluted with cyclohexane (280 ml) at 15–20° C. The crystallized material was filtered and washed with cyclohexane (2×20 ml) to obtain para regioisomer. Yield: 30.7 g.

EXAMPLE 7

Preparation of α,α-dimethyl-4-[4-[4-(hydroxydiphenylmethyl)-1-piperidinyl]-1-oxobutyl] phenylacetic acid, methyl ester 4-(cyclopropylcarbonyl)-α,α-dimethylphenylacetic acid (100 g, 0.43 mol) prepared in accordance with the Example 4 was added to 25% methanolic hydrochloric acid (325 ml) at 20–25° C. The solution was stirred at 40–45° C. for 4 hours and methanol was removed under reduced pressure. The concentrated mass was diluted with water (320 ml) and product was extracted with toluene (2×150 ml). Toluene extract was washed with sodium bicarbonate solution and solvent was removed in vacuo to obtain 120 g of methyl 4-(4-chloro-1-oxobutyl)-α,α-dimethylphenylacetate which was dissolved in methyl isobutyl ketone (480 ml) and treated with 4-(α,α-diphenyl)piperidinemethanol (81 g, 0.30 mol), potassium bicarbonate (196 g, 1.96 mol) and potassium iodide (3.56 g, 0.02 mol) at 96–98° C. for 30 hours. Thereafter, reaction mass was filtered to remove inorganics and the filtrate was concentrated under reduced pressure at 65–70° C. The concentrated mass was dissolved in ethyl acetate (400 ml) and treated with dry hydrochloric acid at 10–15° C. to precipitate the title product as a hydrochloride salt which was isolated by filtration, washed with ethyl acetate (2×80 ml) and dried at 40–45° C. under reduced pressure. Yield: 154 g. mp; 175–181° C.

EXAMPLE 8

Preparation of α,α-dimethyl-4-[4-[4-hydroxydiphenylmethyl)-1-piperidinyl]-1-Hydroxybutyl]phenylacetic acid hydrochloride (terfenadine carboxylate hydrochloride)

To a solution of 154 g of methyl α,α-dimethyl-4-[4-[4-(hydroxydiphenylmethyl)-1-piperidinyl]-1-oxobutyl] phenylacetate hydrochloride prepared in accordance with Example 7 in methanol (460 ml) was added sodium hydroxide (11.21 g, 0.28 mol) at 25–30° C. followed by sodium borohydride (15.8 g, 0.42 mol) in small lots and stirring was continued for 3 hours. The reaction mass was cooled to 10–15° C. and water (390 ml) was added slowly followed by acetic acid (3 ml). Contents were heated to 40–45° C. for 30 min. Thereafter, the product slurry was cooled to 18–20° C., filtered and washed with water (2×100 ml). The product thus obtained was suspended in ethanol (630 ml) and sodium hydroxide (28.8 g, 0.72 mol) dissolved in 120 ml of water was added. Reaction mass was heated at 75–80° C. for 5 hours and thereafter cooled to 15–20° C. and was diluted with water (1260 ml). Concentrated hydrochloric acid was added slowly to lower the pH to 1.8–2.0 to afford the title product which was filtered and washed with water (2×125 ml). It was dried and crystallized from acetone to provide white crystalline terfenadine carboxylate hydrochloride. Yield: 113.67 g. mp: 196–197° C. The product was 99.93% pure and contained 0.03% of meta isomer by HPLC.

HPLC CONDITIONS:

Column: 25 cm long, 4.6 mm internal diameter comprising particles of silica, the surface of which has been modified by chemically bonded octadecylsilyl groups; particle size: 5 μm; column temperature: ambient Detection wavelength: 215 nm Mobile Phase: Mixture of buffer pH 2.5 and methanol in the ratio of 40:60 v/v. Buffer of pH 2.5 was prepared by dissolving 1.17 g of 1-octanesulphonic acid sodium salt and 1 ml of triethylamine in 1000 ml water and pH adjusted to 2.5 with orthophosphoric acid.

We claim:

1. A process to obtain pure 4-(cyclopropylcarbonyl)-α,α-dimethylphenylacetic acid of Formula I comprising the steps of:

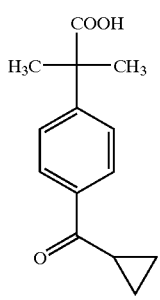

Formula I dissolving a mixture of para and meta regioisomers of Formula VIII in a crystallization solvent selected from the group consisting of a hydrocarbon and an ether to obtain a solution,

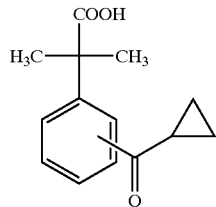

Mixture of para and meta regioisomers of Formula VIII optionally seeding the said solution with a small quantity of pure para isomer of Formula I, cooling the said solution to obtain selectively crystallized isomer of Formula I such that the amount of meta isomer of Formula II in the said crystallized isomer of Formula I is below 0.5% by weight.

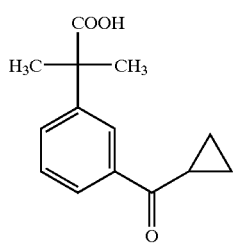

Formula II

2. The process according to claim 1 wherein the said crystallization solvent is selected from the group consisting of hexane, heptane, cyclohexane, diethyl ether, diisopropyl ether and mixtures thereof.

3. The process according to claim 1 wherein the said crystallization solvent is cyclohexane.

4. A process to produce para-isomerically pure terfenadine carboxylate of Formula III comprising the steps of:

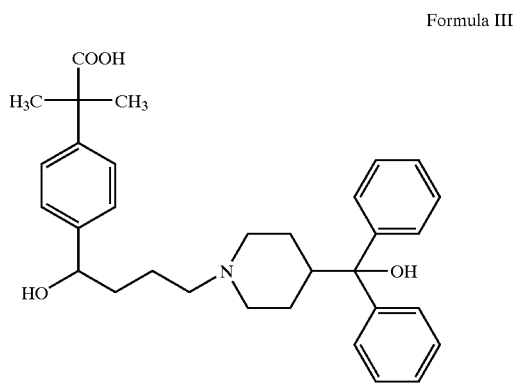

Formula III dissolving a mixture of para and meta regioisomers of Formula VIII in a crystallization solvent is selected from the group consisting of a hydrocarbon and an ether to obtain a solution,

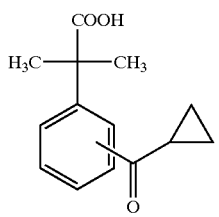

Mixture of para and meta regioisomers of Formula VIII optionally seeding the said solution with a small quantity of pure para isomer of Formula I, cooling the said solution to obtain selectively crystallized isomer of formula I

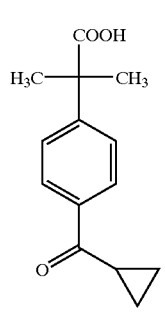

Formula I such that the amount of meta isomer of Formula II in the said crystallized isomer of Formula I is below 0.5% by weight, reacting the said crystallized isomer of Formula I with a piperidine compound of Formula IV to form the piperidine derivative compound of Formula Xl,

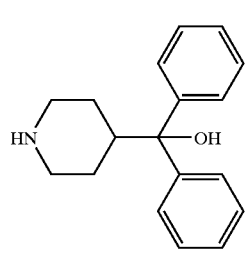

Formula IV

-continued

Formula XI

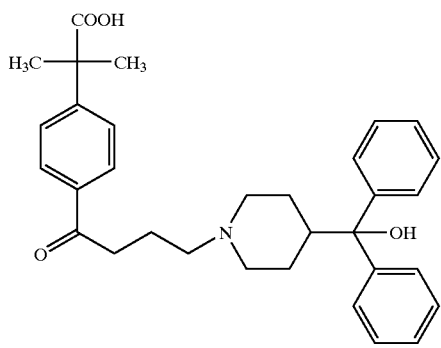

reacting the keto group of the compound of Formula Xl to convert it to a hydroxyl group by reduction reaction to obtain a terfenadine carboxylate of Formula III that contains less than 0.1% of meta regioisomer.

5. The process according to claim 4 wherein the said crystallization solvent is selected from the group consisting of hexane, heptane, cyclohexane, diethyl ether, diisopropyl ether and mixtures thereof.

6. The process according to claim 4 wherein the said crystallization solvent is cyclohexane.

* * * * *